(12) United States Patent
Yang et al.

(10) Patent No.: US 12,146,864 B1
(45) Date of Patent: Nov. 19, 2024

(54) DEVICE AND METHOD FOR EVALUATING DAMAGE TO SURROUNDING ROCK POROUS STRUCTURE DUE TO HIGH-TEMPERATURE AND HIGH-HUMIDITY GAS

(71) Applicant: CHINA UNIVERSITY OF MINING AND TECHNOLOGY, BEIJING, Beijing (CN)

(72) Inventors: Liu Yang, Beijing (CN); Shuo Wang, Beijing (CN); He Liu, Beijing (CN)

(73) Assignee: CHINA UNIVERSITY OF MINING AND TECHNOLOGY, BEIJING, Beijing (CN)

( * ) Notice: Subject to any disclaimer, the term of this patent is extended or adjusted under 35 U.S.C. 154(b) by 0 days.

(21) Appl. No.: 18/658,973

(22) Filed: May 8, 2024

(30) Foreign Application Priority Data

May 8, 2023 (CN) .......................... 202310508856.9

(51) Int. Cl.
*G01N 3/12* (2006.01)
*G01N 3/06* (2006.01)
(Continued)

(52) U.S. Cl.
CPC ................. *G01N 3/12* (2013.01); *G01N 3/06* (2013.01); *G01N 3/18* (2013.01); *G01N 33/24* (2013.01);
(Continued)

(58) Field of Classification Search
CPC .. G01N 3/12; G01N 3/06; G01N 3/18; G01N 33/24; G01N 2203/006; G01N 2203/0226; G01N 2203/0298; G01N 2203/0641
See application file for complete search history.

(56) References Cited

U.S. PATENT DOCUMENTS

| 10,061,061 | B2 * | 8/2018 | Ziauddin | ................. E21B 43/25 |
| 10,724,972 | B2 * | 7/2020 | Caliskan | ................. F16C 13/04 |

(Continued)

FOREIGN PATENT DOCUMENTS

| CN | 104931403 A | 9/2015 |
| CN | 107590349 A | 1/2018 |

(Continued)

OTHER PUBLICATIONS

Zhu Hanqing, et al., Nanopore structure characteristics of shale based on Ar adsorption, Lithologic Reservoirs, 2018, pp. 77-84, vol. 30, No. 2.

(Continued)

*Primary Examiner* — Freddie Kirkland, III
(74) *Attorney, Agent, or Firm* — Bayramoglu Law Offices LLC (57) ABSTRACT

A device and a method for evaluating damage of high-temperature and high-humidity gas to a surrounding rock porous structure are provided. The device includes a rock sample clamper, a temperature control device, a pressurizing device, a gas mixing injection device, a CT scanning device and a low-temperature nitrogen adsorption device. By simulating the gas rock reaction under the conditions of in-situ temp., pressure and gas, using CT scanning device to visually monitor and analyze the reaction condition of gas and tunnel surrounding rock and the change condition of porous structure, and using low-temperature nitrogen adsorption test to obtain porous structure parameters change condition before and after reaction of gas and tunnel surrounding rock, and the damage evaluation index of the porous structure is established.

4 Claims, 7 Drawing Sheets

(51) Int. Cl.
*G01N 3/18* (2006.01)
*G01N 33/24* (2006.01)

(52) U.S. Cl.
CPC .............. *G01N 2203/006* (2013.01); *G01N 2203/0226* (2013.01); *G01N 2203/0298* (2013.01); *G01N 2203/0641* (2013.01)

(56) References Cited

U.S. PATENT DOCUMENTS

| | | | |
|---|---|---|---|
| 11,579,333 B2* | 2/2023 | Almarzooq | E21B 49/02 |
| 11,948,284 B2* | 4/2024 | Song | G06T 17/00 |
| 12,019,038 B2* | 6/2024 | Sandu | G01N 33/28 |
| 2016/0025895 A1* | 1/2016 | Ziauddin | G01V 20/00 |
| | | | 702/11 |

FOREIGN PATENT DOCUMENTS

| | | |
|---|---|---|
| CN | 108458957 A | 8/2018 |
| CN | 207991936 U | 10/2018 |
| CN | 111896565 A | 11/2020 |
| CN | 112284923 A | 1/2021 |
| CN | 113109182 A | 7/2021 |
| WO | 2016168882 A1 | 10/2016 |
| WO | 2022056944 A1 | 3/2022 |

OTHER PUBLICATIONS

Yu Wang, et al., Introduction on 1.1 Role of Industrial CT Scanning in Rock Mechanics 1.2 Overview of the application of industrial CT technology in rock mechanics, Rock Mass Mesostructural Mechanics Industrial CT Technology and Application, 2021, pp. 1-17.

Bingsong Yu, et al., Depositional environments and diagenesis of organic-rich shales, 5. CT scan, 2016, pp. 217-219.

* cited by examiner

DEVICE AND METHOD FOR EVALUATING DAMAGE TO SURROUNDING ROCK POROUS STRUCTURE DUE TO HIGH-TEMPERATURE AND HIGH-HUMIDITY GAS

CROSS-REFERENCE TO THE RELATED APPLICATIONS

This application is based upon and claims priority to Chinese Patent Application No. 202310508856.9, filed on May 8, 2023, the entire contents of which are incorporated herein by reference.

TECHNICAL FIELD

The invention relates to the technical field of surrounding rock micro-structure analysis, especially relates to a device and method for evaluating damage to surrounding rock porous structure due to high-temperature and high-humidity gas.

BACKGROUND

Deep coal rock, shale and mud sandstone and soft rock stratum mine, tunnel excavation, working surface temperature is as high as 35° C. to 40° C., relative humidity is more than 95%. The excavation work under high-temperature and high-humidity environment will cause the porous adsorption gas (methane, carbon dioxide and sulphur-containing gas and so on) to be moved abnormally, and the deep moist heat disaster is intensified. The research shows that the deep soft rock poison gas is transported in the geological environment such as excavation, unloading, high-temperature and multi-phase seepage. The high-temperature and high-humidity gas in the deep engineering not only seriously influences the physical and mental health of the worker, but also causes the surrounding rock strength to soften, and induces the large deformation disaster and secondary disaster. At present, the influence of the high-temperature and high-humidity gas on the softening of the surrounding rock is mainly focused on the research on the macroscopical mechanical property, the research on the microcosmic structure change of the surrounding rock is lacked, and the visual research means is lacked at the same time.

SUMMARY

To solve the problems present in prior techniques, this invention proposes the following technical solutions: in order to solve the problem in the existing technology, the invention provides the following technical solution.

The first aspect of the invention provides a device for evaluating damage to surrounding rock porous structure by high-temperature and high-humidity gas, comprising: a rock sample clamper, a temperature control device, a pressurizing device, a gas mixing injection device, a CT scanning device and a low-temperature nitrogen adsorption device;

The rock sample clamper is used for placing and clamping the rock sample, the rock sample comprises a broken block and a surrounding rock formed by simulating tunnel excavation, a simulation tunnel is formed between the broken block and the surrounding rock, a simulation excavation cutter line is formed on the surrounding rock formed by simulating excavation;

The temperature control device is used for providing the in-situ temperature for the rock sample; the pressurizing device is used for providing in-situ pressure for the rock sample; the gas mixing injection device is used for providing in-situ gas for the rock sample;

The CT scanning device is used for scanning the rock sample structure before and after the gas injection, so as to visually monitor and analyze the gas transport path and the porous structure change, so as to perform qualitative evaluation on the damage to the surrounding rock porous structure under the action of high-temperature and high-humidity gas;

The low-temperature nitrogen adsorption device is used for performing low-temperature nitrogen adsorption test on the surrounding rock formed by simulation excavation before and after gas injection, so as to utilize the combination of test data and fractal theory, to obtain the index for quantitatively evaluating the damage degree of the surrounding rock porous structure under the action of high-temperature and high-humidity gas: porous complexity change rate and porous volume change rate, so as to perform quantitative evaluation.

Preferably, the device further comprises: a tail gas separating device, a gas chromatograph and a conductivity meter, the tail gas separating device is used for performing gas-liquid separation on the tail gas, the gas chromatograph is used for detecting the gas component obtained by gas-liquid separation, the conductivity meter is used for detecting the conductivity of the liquid obtained by gas-liquid separation.

The second aspect of the invention provides a method for evaluating damage to surrounding rock porous structure by high-temperature and high-humidity gas, using the device of the first aspect, the method comprises:

Making rock sample;

Fixing the rock sample in the rock sample clamper;

Applying an in-situ temperature and pressure to the rock sample, and injecting an in-situ gas so that the gas reacts with the rock sample;

The CT scanning device is used for visually monitoring and analyzing the gas moving path in the gas rock reaction and the porous structure change before and after the reaction so as to qualitatively evaluate the damage to the surrounding rock porous structure under the action of high-temperature and high-humidity gas;

Respectively performing low-temperature nitrogen adsorption test to the surrounding rock before and after the gas rock reaction to obtain the change of the related parameters of the porous structure;

Calculating the porous complexity change rate and the porous volume change rate according to the change of the related parameter of the porous structure, and quantitatively evaluating the damage to the surrounding rock porous structure according to the porous complexity change rate and/or the porous volume change rate.

Preferably, the method further comprises:

Performing gas-liquid separation on the gas at the tail end to obtain gas and liquid, The gas component is detected and the conductivity of the liquid is detected.

Preferably, the manufacturing of the rock sample comprises:

Cutting the plunger sample at the centre of the standard rock core, and taking the rest part as the surrounding rock sample; the section between the plunger sample and the surrounding rock sample is used for simulating the section between the broken rock body and the surrounding rock in the tunnel excavation.

Preferably, the CT scanning device is used to visually monitor and analyze the gas transport path in the gas rock reaction and the porous structure change before and after the reaction, so as to perform qualitative evaluation on the damage to the surrounding rock porous structure under the action of high-temperature and high-humidity gas, comprising:

Using the CT scanning device to respectively scan the rock sample before and after the gas rock reaction to obtain the CT scanning image of the cross section of the rock sample along different positions;

Comparing the CT scanning image of the cross section of the same position of the rock sample before and after the gas rock reaction, obtaining the gas moving path in the gas rock reaction;

According to the gas transport path analysis to obtain the porous structure change before and after the reaction;

According to the change of the porous structure, qualitatively evaluating the damage to the surrounding rock porous structure under the action of high-temperature and high-humidity gas.

Preferably, the step of calculating the porous complexity change rate according to the change of the related parameters of the porous structure comprises:

$$\frac{V}{V_m} = K\left(RT\ln\left(\frac{P_0}{P}\right)\right)^{-(3-D)},$$

$$\sigma_1 = \frac{D_I}{D_E},$$

In the formula, V is the gas adsorption volume under balance pressure P, $V_m$ is a layer of gas adsorption volume, V and $V_m$ are obtained by low-temperature nitrogen adsorption test, K is characteristic constant, R is gas constant, T is absolute temperature, $P_0$ is saturated vapour pressure of nitrogen at liquid nitrogen temperature, D is fractal dimension, $\sigma_1$ is the porous complexity change rate, $D_I$ is the fractal dimension before the gas rock reaction, $D_E$ is the fractal dimension after the gas rock reaction, $P_0/P$ is the damage coefficient.

Preferably, the step of calculating the porous volume change rate according to the change of the porous structure related parameters comprises:

$$K_1 = \frac{|V_{p1} - V_{p2}|}{V_{p1}} \times 100\%$$

In the formula, $K_1$ is the porous volume change rate, $V_{P1}$ is the porous volume before the gas rock reaction, $V_{P2}$ is the porous volume after the gas rock reaction, $V_{P1}$ and $V_{P2}$ are obtained by low-temperature nitrogen adsorption test.

Preferably, the method further comprises:

Using the low-temperature nitrogen adsorption test to obtain the gas adsorption-desorption curve before and after the gas rock reaction;

Judging the porous type according to the shape of the gas adsorption-desorption curve;

Judging the change of the porous shape before and after the gas rock reaction according to the porous type;

Evaluating the damage condition of the surrounding rock porous structure according to the change of the porous shape.

The beneficial effects of the present invention are as follows: The device and method for evaluating damage to surrounding rock porous structure by high-temperature and high-humidity gas provided by the invention, by simulating the in-situ temperature, gas rock reaction under pressure and gas condition, using CT scanning device to visually monitor and analyze the reaction condition of gas and rock sample and the change condition of porous structure, using low-temperature nitrogen adsorption test to obtain the change condition of porous structure parameter before and after the reaction of gas and tunnel surrounding rock, establishing the damage evaluation index of the porous structure, realizing the damage evaluation of the high-temperature and high-humidity gas to the tunnel surrounding rock porous structure in the tunnel excavation process, at the same time, can effectively obtain the gas saturation characteristic of different tunnel section, effectively supplement the gas caused by the rock mechanical strength, structure softening research.

In the figure, the meaning of each symbol is as follows:
1—rock sample clamper, 2—temperature control device, 3—pressurizing device, 4—gas mixing injection device, 5—CT scanning device, 6—low-temperature nitrogen adsorption device, 7—rock sample, 8—tail gas separating device, 9—gas chromatograph, 10—conductivity meter, 11—air compressor, 12—nitrogen bottle, 13—adsorption instrument, 14—adsorption instrument computer controller, 15—cutting simulated tunnel section, 16—cutting feed line, 17—simulated tunnel surrounding rock structure.

DETAILED DESCRIPTION OF THE EMBODIMENTS

In order to better understand the above technical solution, the above technical solution will be described in detail below with reference to the accompanying drawings and specific embodiments.

Aiming at the problem in the existing technology, the invention Claims a device and method for evaluating damage of high-temperature and high-humidity gas to surrounding rock porous structure. The device mainly uses X ray computer tomography (CT) as the main monitoring device, loading rock sample clamper, temperature control device, pressurizing device, gas mixing injection device, tail gas separating device, gas chromatograph and conductivity meter, furthest simulating the original stratum temperature, the pressure environment visually monitors the reaction and transportation of the gas. The rock sample is cut into the tunnel section shape on the microcosmic scale, the gas is injected into the crack of the cutting sample through the clamp fastener, the reaction process of the tunnel gas and the cutting surface (the outer surface of the tunnel surrounding rock) is simulated. in addition, the surrounding rock (simulated surrounding rock) before and after gas injection is subjected to low-temperature nitrogen adsorption test through the low-temperature nitrogen adsorption device, to obtain the parameter change of the micro-porous structure of the surrounding rock before and after gas-surrounding rock reaction, combined with fractal theory to obtain the damage index for quantitatively evaluating the surrounding rock under the action of high-temperature and high-humidity gas, so as to quantitatively evaluate the damage to the surrounding rock porous structure by the high-temperature and high-humidity gas in the tunnel excavation process.

Embodiment 1

Figure 1:
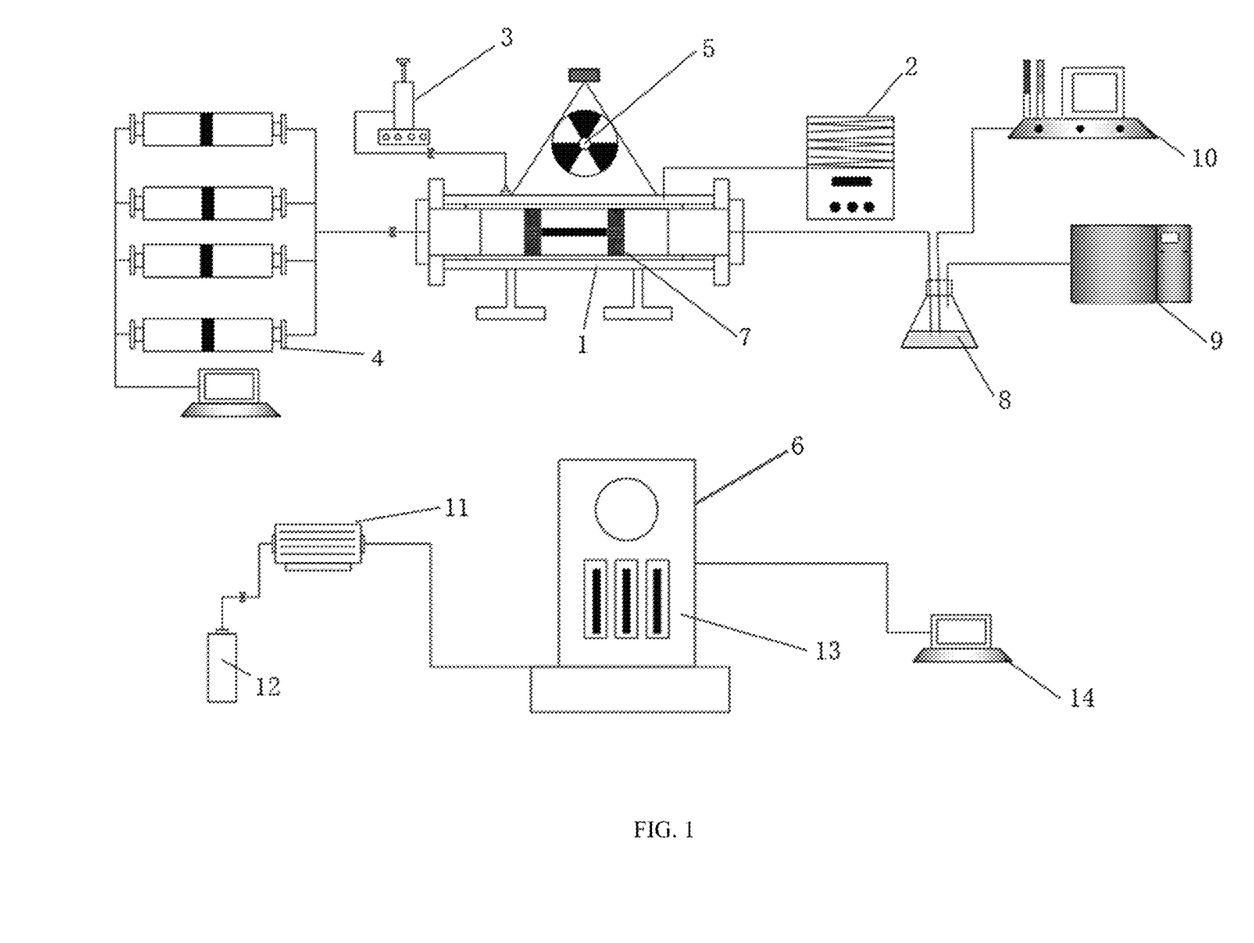
FIG. 1 is a schematic diagram of the structure of the device for evaluating damage of the high-temperature and high-humidity gas to the surrounding rock porous structure according to the present invention.

As shown in FIG. 1, the embodiment of the present invention provides a device for evaluating damage to the surrounding rock porous structure by high-temperature and high-humidity gas, comprising: a rock sample clamper 1, a temperature control device 2, a pressurizing device 3, a gas mixing injection device 4, a CT scanning device 5 and a low-temperature nitrogen adsorption device 6.

The rock sample clamper 1 is used for placing and clamping the rock sample 7, the rock sample 7 is used for simulating tunnel excavation, the rock sample comprises a crushed block and surrounding rock formed by simulating excavation, between the crushed block and surrounding rock is formed with a simulation tunnel, the surrounding rock is formed with a simulation excavating cutter line.

The temperature control device 2 is used for providing in-situ temperature for the rock sample 7; the pressurizing device 3 is used for providing in-situ pressure for the rock sample 7; The gas mixing injection device 4 is used for providing in-situ gas for the rock sample 7.

The CT scanning device 5 is used for scanning the rock sample structure before and after the gas injection, so as to visually monitor and analyze the gas transport path and porous structure change, so as to perform qualitative evaluation on the damage to the surrounding rock under the action of high-temperature and high-humidity gas.

The low-temperature nitrogen adsorption device 6 is used for performing low-temperature nitrogen adsorption test on the surrounding rock before and after gas injection, so as to utilize the test data to combine with fractal theory, to obtain the damage degree index for quantitative evaluation of surrounding rock under the action of high-temperature and high-humidity gas: porous complexity change rate and porous volume change rate, so as to perform quantitative evaluation.

The device for evaluating damage to surrounding rock porous structure by high-temperature and high-humidity gas provided by the invention further comprises: a tail gas separating device 8, a gas chromatograph 9 and a conductivity meter 10, the tail gas separating device 8 is used for performing gas-liquid separation on the tail gas, the gas chromatograph 9 is used for detecting the gas component obtained by gas-liquid separation, the conductivity meter 10 is used for detecting the conductivity of the liquid obtained by gas-liquid separation.

In the use process, the rock sample can be selected from the cylinder, by performing internal cutting on the rock sample, a plunger sample of a small cylinder is cut from the centre, the plunger sample part can simulate the whole gravel structure in the tunnel excavation process, the rest part of the rock sample except the small plunger sample can be used as the surrounding rock sample, The surrounding rock sample can be used for simulating the whole tunnel surrounding rock structure. then putting the plunger sample into the surrounding rock sample to obtain the rock sample whole body, and putting the whole structure into the rock sample clamper. The in-situ pressure and temperature of the rock sample are provided by the temperature control device and the pressurizing device, and then the tunnel original gas is injected into the rock sample by the gas mixing injection device at the injection end. The suction end of the gas mixing injection device is connected with multiple gases, including air, methane, carbon dioxide and sulphur-containing gas, so as to simulate the mixed gas type in the tunnel excavation; The mixed gas mainly moves along the cutting surface in the rock sample (the gap between the plunger sample and the surrounding rock sample, namely the outer arc profile surface of the tunnel), and the gas reacts with the rock on the cutting surface. at the same time, the CT scanning device performs quantitative visual monitoring on the gas transport path and the saturation characteristic, and analyzes the change of the surrounding rock porous structure according to the monitored result. after the tail gas is discharged, the tail gas separating device can be used for condensing and separating the gas and liquid, and then the separated liquid is monitored by electrical conductivity, the ion concentration change is analyzed, and the gas obtained by separating is analyzed by gas chromatograph.

In addition, the surrounding rock sample can be subjected to low-temperature nitrogen adsorption test by using a low-temperature nitrogen adsorption device before and after the reaction between the gas and the rock sample, so as to obtain the porous size, gap volume of the surrounding rock porous structure before and after the gas rock reaction, The test data of parameters such as porous shape and so on, and then the test data are combined with fractal theory to establish a damage degree index for quantitative evaluation of surrounding rock under the action of high-temperature and high-humidity gas: the porous complexity change rate and the porous volume change rate, finally using the two damage index to quantitatively evaluate the damage condition of the high-temperature and high-humidity gas to the surrounding rock in the tunnel excavation process. Wherein, the low-temperature nitrogen adsorption device may include: an air compressor 11, a nitrogen bottle 12, an adsorption instrument 13 and an adsorption instrument computer controller 14.

Embodiment 2

The embodiment of the invention provides a method for evaluating damage to surrounding rock porous structure by high-temperature and high-humidity gas, using the device according to embodiment 1, the method comprising: making rock sample; fixing the rock sample in the rock sample clamper; applying an in-situ temperature and pressure to the rock sample, and injecting an in-situ gas so that the gas reacts with the rock sample; the CT scanning device is used for visually monitoring and analyzing the gas transport path in the gas rock reaction and the porous structure change before and after the reaction so as to qualitatively evaluate the damage to the surrounding rock under the high-temperature and high-humidity gas; respectively performing low-temperature nitrogen adsorption test to the surrounding rock sample before and after the gas rock reaction to obtain the change of the related parameters of the porous structure; calculating the porous complexity change rate and the porous volume change rate according to the change of the relative parameters of the porous structure, and quantitatively evaluating the damage to the surrounding rock structure according to the porous complexity change rate and/or the porous volume change rate.

The method for evaluating damage of high-temperature and high-humidity gas to surrounding rock porous structure provided by the embodiment of the invention further comprises: performing gas-liquid separation to the gas at the tail end to obtain gas and liquid, and detecting the conductivity of the gas component and the liquid.

Figure 2:
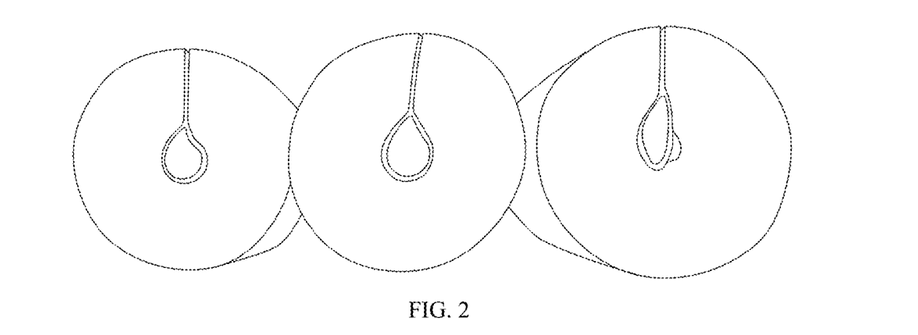
FIG. 2 is a sectional view of a real rock sample cut.
Figure 3:
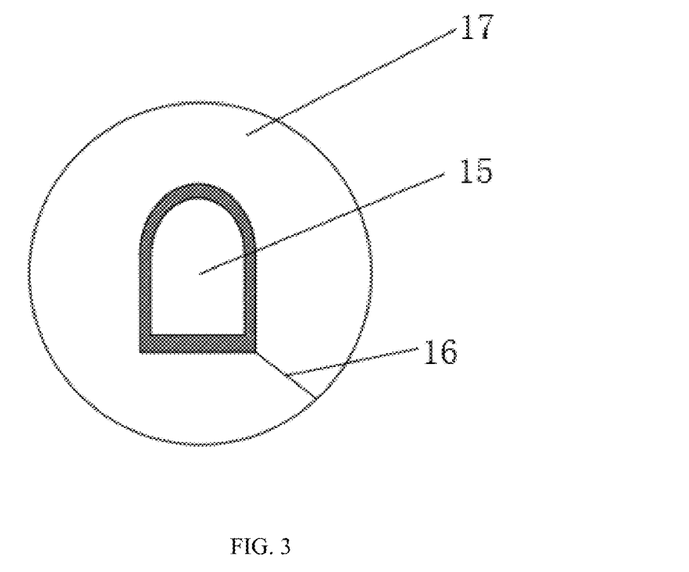
FIG. 3 is a schematic view of the cross section of the rock sample.

Wherein, the rock sample can be made according to the following method: a plunger sample (such as a cylinder with a diameter of 0.5 cm and a length of 5 cm) is cut at the center of the standard core (such as a cylinder with a diameter of 2.5 cm and a length of 5 cm), and the remainder is used as a surrounding rock sample; wherein the plunger sample is used for simulating the whole fragment structure in the tunnel excavation, the surrounding rock sample is used for simulating the surrounding rock in the tunnel excavation, the gap between the plunger sample and the surrounding rock sample is used for simulating the tunnel in the tunnel excavation. The cross section of the rock sample can be shown in FIG. 2, and the cross section structure of the rock sample can be shown in FIG. 3, FIG. 3 included cutting simulated tunnel section 15, cutting feed line 16 and simulated tunnel surrounding rock structure 17.

In the embodiment of the invention, the CT scanning device is used to visually monitor and analyze the gas transport path in the gas rock reaction and the porous structure change before and after the reaction, so as to perform qualitative evaluation on the damage to the surrounding rock under the action of high-temperature and high-humidity gas, comprising: using the CT scanning device to respectively scan the rock sample before and after the gas rock reaction to obtain the CT scanning image of the cross section of the rock sample along different positions; comparing the CT scanning image of the cross section of the same position of the rock sample before and after the gas rock reaction, obtaining the gas moving path in the gas rock reaction; according to the gas transport path analysis to obtain the porous structure change before and after the surrounding rock reaction; qualitatively evaluating the damage to the surrounding rock under the action of high-temperature and high-humidity gas according to the change of the porous structure.

The CT scanning data can be used to obtain the gas transport path by qualitative or quantitative method. The qualitative method is: In the CT scanning image, the gas and the surrounding rock skeleton are displayed in different colours, and the gas moving path can be obtained by observing the CT scanning image. The quantification method is as follows: obtaining the gas saturation of different section positions of the surrounding rock according to the CT scanning data, and then analyzing the gas saturation of different section positions to obtain the gas moving path.

In the embodiments of the present invention, the calculation of the porous complexity change rate according to the change of the parameters related to the porous structure may include:

$$\frac{V}{V_m} = K\left(RT\ln\left(\frac{P_0}{P}\right)\right)^{-(3-D)},$$

$$\sigma_1 = \frac{D_I}{D_E},$$

In the formula, V is the gas adsorption volume under balance pressure P, $V_m$ is a layer of gas adsorption volume, V and $V_m$ are obtained by low-temperature nitrogen adsorption test, K is characteristic constant, R is gas constant, T is absolute temperature, $P_0$ is saturated vapour pressure of nitrogen at liquid nitrogen temperature, D is fractal dimension, $\sigma_1$ is the porous complexity change rate, $D_I$ is the fractal dimension before the gas rock reaction, $D_E$ is the fractal dimension after the gas rock reaction, $P_0/P$ is the damage coefficient.

The porous volume change rate is calculated according to the change of the related parameters of the porous structure, and the adopted calculation formula comprises:

$$K_1 = \frac{|V_{p1} - V_{p2}|}{V_{p1}} \times 100\%,$$

In the formula, $K_1$ is the porous volume change rate, $V_{P1}$ is the porous volume before the gas rock reaction, $V_{P2}$ is the porous volume after the gas rock reaction, $V_{P1}$ and $V_{P2}$ are obtained by low-temperature nitrogen adsorption test.

In a preferred embodiment of the present invention, the method for evaluating the damage of the high-temperature and high-humidity gas to the surrounding rock porous structure may also include: using the low-temperature nitrogen adsorption test to obtain the gas adsorption-desorption curve before and after the gas rock reaction; judging the porous type according to the shape of the gas adsorption-desorption curve; judging the change of the porous shape before and after the gas rock reaction according to the porous type; according to the change of the porous shape, evaluating the surrounding rock damage condition.

In a specific embodiment, the device of the invention can be used for evaluating the damage of the high-temperature and high-humidity gas to the surrounding rock porous structure according to the following steps and calculation method.

Step 1, cutting the standard core (2.5 cm in diameter and 5 cm in length) by linear cutting, cutting a small plunger sample (0.5 cm in diameter and 5 cm in length) in the centre of the standard core, and taking the remaining part as the surrounding rock sample.

Step two, putting the prepared surrounding rock sample into a drying box to dry for 24 hours, then taking out and standing, then putting the surrounding rock sample into a low-temperature nitrogen adsorption device to measure, obtaining various parameters of the porous structure such as porous diameter, porous volume, gas adsorption volume and so on.

Step three, after the test is finished, the plunger sample is placed back to the taken out surrounding rock sample, then the whole rock sample is placed in the rock sample clamper, the rock sample clamper is added with the confining pressure and temperature under the stratum condition, at the same time, the rock sample is performed with gas mixing injection, The CT scanning device is used for scanning the rock sample before and after the gas rock reaction to obtain the CT scanning image of the cross section of the rock sample along different positions.

Step four, when the air pressure at the tail end is stable, closing the inlet and outlet valve, standing for 24 hours, making the gas react with the porous structure.

Step five, after standing, opening the valve at the tail end, introducing the gas into the gas-liquid separating device, then accessing the gas into the gas chromatograph for gas component analysis, accessing the liquid into the conductivity meter for testing the conductivity.

Step 6, taking out the rock sample after the experiment, after standing for 12 hours, putting the rock sample in a low-temperature nitrogen adsorption device for measurement, obtaining various parameters of the porous structure after the reaction.

Sorting and analyzing the data obtained by the experiment, and evaluating the surrounding rock damage.

The analysis method of data adopted by the invention mainly comprises two kinds, one is in the process of rock sample-gas action, through CT online scanning, extracting CT slice graph to perform porous structure visualization analysis, the analysis method mainly monitors the process of gas rock sample reaction from microcosmic angle. the radioactive source in the CT device can emit X ray in the scanning process, most of the X ray can pass through the whole structure of the rock sample, scanning the whole rock sample structure, respectively performing CT scanning before and after the rock sample gas injection, by comparing the CT slice image before and after the gas injection, It can obtain the change condition of the porous structure at the same position of the rock sample structure.

Figure 4A:
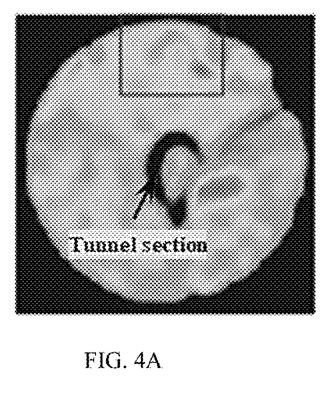
FIGS. 4A-4H show a CT scanning slice diagram of the cross section of the rock sample at different positions before and after the gas rock reaction.
Figure 4B:
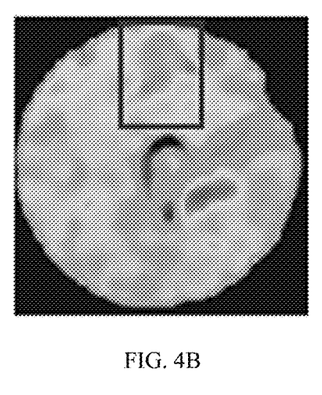
Figure 4C:
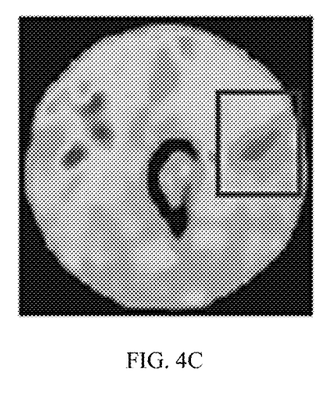
Figure 4D:
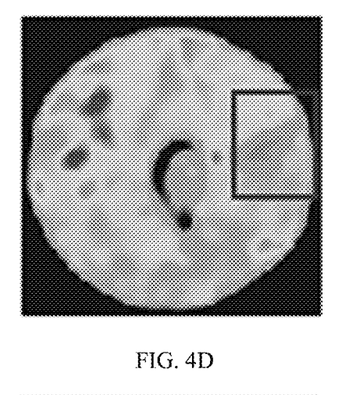
Figure 4E:
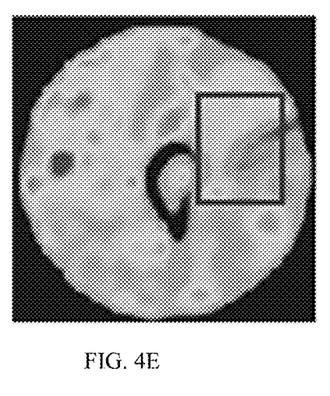
Figure 4F:
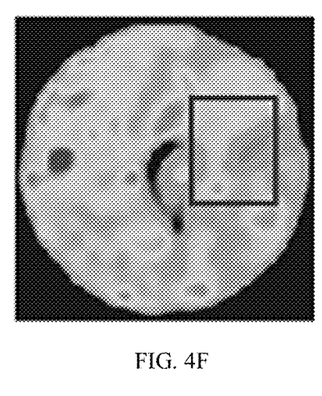
Figure 4G:
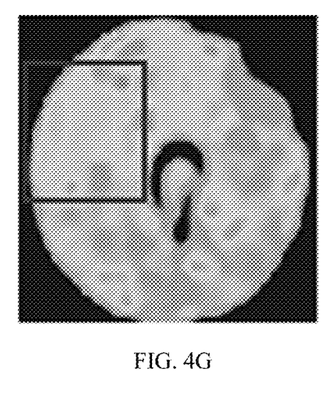
Figure 4H:
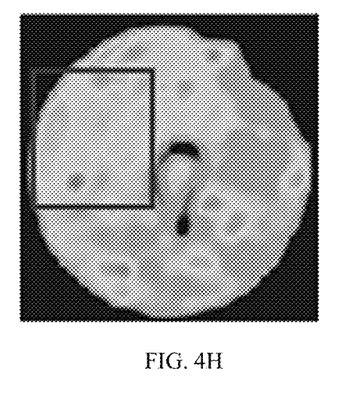

As shown in FIGS. 4A-4H, a CT scanning slice diagram of four section positions is shown, wherein FIG. 4A and FIG. 4B respectively show a CT slices 1 before and after gas injection of the first section position of the rock sample, FIG. 4C and FIG. 4D show CT slices 2 before and after gas injection of the second cross-sectional position of the rock sample, respectively, FIG. 4E and FIG. 4F show CT slices 3 before and after gas injection of the third cross-sectional position of the rock sample, respectively, FIG. 4G and FIG. 4H show CT slices 4 before and after gas injection in the fourth cross-sectional position of the rock sample, respectively. In comparison with FIG. 4A and FIG. 4B, it can be seen that the upper structure of the rock sample is grey before the gas injection, which is caused by the different spatial variability of the rock sample material itself, and after the gas injection, the grey degree of the same position is deepened, and the range of the grey area is increased, This shows that the structure is damaged. Therefore, the following conclusions can be obtained by comparing the CT scanning slice images before and after the gas injection: The upper structure of the tunnel section is damaged after the high-temperature and high-humidity gas is met. The overall structure of the tunnel surrounding rock can be analyzed and evaluated by analyzing the picture data of the CT scan (such as the CT scan slice diagram in FIGS. 4A-4H).

The second type data analysis method is used for quantitatively analyzing the damage to the porous structure, innovatively providing a method for performing low-temperature nitrogen adsorption measurement before and after the gas rock reaction, at the same time, combining the adsorption test data with the fractal theory, establishing a method for evaluating the damage degree of the surrounding rock under the action of high-temperature and high-humidity gas. The damage degree evaluation is mainly based on two indexes, one of which is the porous complexity change rate. Firstly, the fractal dimension is calculated based on the fractal theory, and then the porous complexity change rate is calculated by the fractal dimension before and after the gas injection. In the specific implementation process, the surrounding rock sample can be subjected to low-temperature nitrogen adsorption test before and after the gas injection, and the adsorption data before and after the reaction is extracted, and then the fractal dimension before and after the gas injection is calculated by using these data. The larger the fractal dimension, the more complex the porous structure. Specifically, the calculation can be performed by the following formula:

$$\frac{V}{V_m} = K\left(RT\ln\left(\frac{P_0}{P}\right)\right)^{-(3-D)}$$

$$\sigma_1 = \frac{D_I}{D_E}$$

In the formula, V is gas adsorption volume under balance pressure P, $V_m$ is a layer of gas adsorption volume, V and $V_m$ are obtained by low-temperature nitrogen adsorption test, K is characteristic constant, R is gas constant, T is absolute temperature (T=77.36K), $P_0$ is saturated nitrogen pressure ($P_0$=100.74 KPa), D is fractal dimension, $\sigma_1$ is porous complexity change rate, $D_I$ is the fractal dimension before gas rock reaction, $D_E$ is the fractal dimension after gas rock reaction.

In the specific calculation process, The following formula is obtained by deformation $$\frac{V}{V_m} = K\left(RT\ln\left(\frac{p_0}{p}\right)\right)^{-(3-D)} : \ln V = C + \alpha\ln\left(\ln\left(\frac{p_0}{p}\right)\right)$$

$$D = \alpha + 3$$

Using formula ln $$V = C + \alpha\ln\left(\ln\left(\frac{p_0}{p}\right)\right),$$

the fitting curve can be obtained, wherein C is the intercept of the fitting curve, and α is the slope of the fitting curve. The fractal dimension can be calculated according to the slope a of the fitting curve, comprising calculating the fractal dimension $D_I$ before the reaction and the fractal dimension $D_E$ after the reaction, and finally calculating the porous complexity change rate $\sigma_1$.

The damage degree of the surrounding rock can be evaluated according to the porous complexity change rate. For example, in one example, the relationship between the porous complexity change rate and the surrounding rock damage degree is shown in Table 1. It should be noted that, Table 1 is the relationship between the the porous complexity change rate and the damage degree of part of the surrounding rock tested, and does not represent the distribution range of the the porous complexity change rate and the damage degree of all the surrounding rock, and is only used for reference.

TABLE 1

| $\sigma_1$ (%) | Damage degree |
|---|---|
| $0 < \sigma_1 < 1$ | No |
| $1 \leq \sigma_1 < 5$ | Weak |
| $5 \leq \sigma_1 < 10$ | Strong |
| $10 \leq \sigma_1 < 20$ | Super strong |

The other index of the damage degree evaluation is the porous volume change rate. the reaction degree of the high-temperature and high-humidity gas and the inner and outer surfaces of the tunnel is researched by comparing the porous volume change before and after the gas rock reaction; Therefore, the damage degree of porous structure can be reacted by calculating the porous volume change rate.

The porous volume change rate can be calculated by the following formula:

$$K_1 = \frac{|V_{p1} - V_{p2}|}{V_{p1}} \times 100\%$$

In the formula, $K_1$ is the porous volume change rate, $V_{P1}$ is the porous volume before the gas rock reaction, $V_{P2}$ is the porous volume after the gas rock reaction, $V_{P1}$ and $V_{P2}$ are obtained by low-temperature nitrogen adsorption test.

Figure 5:
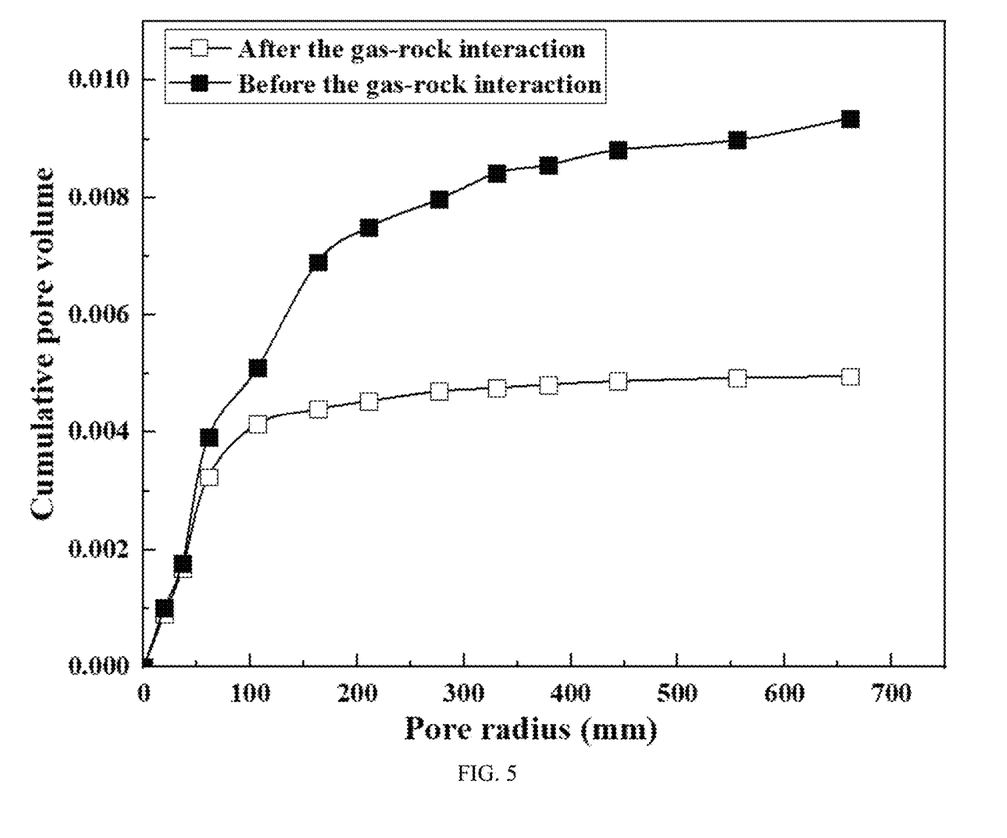
FIG. 5 is a schematic diagram of the porous volume variation of the growth type after the gas rock reaction.
Figure 6:
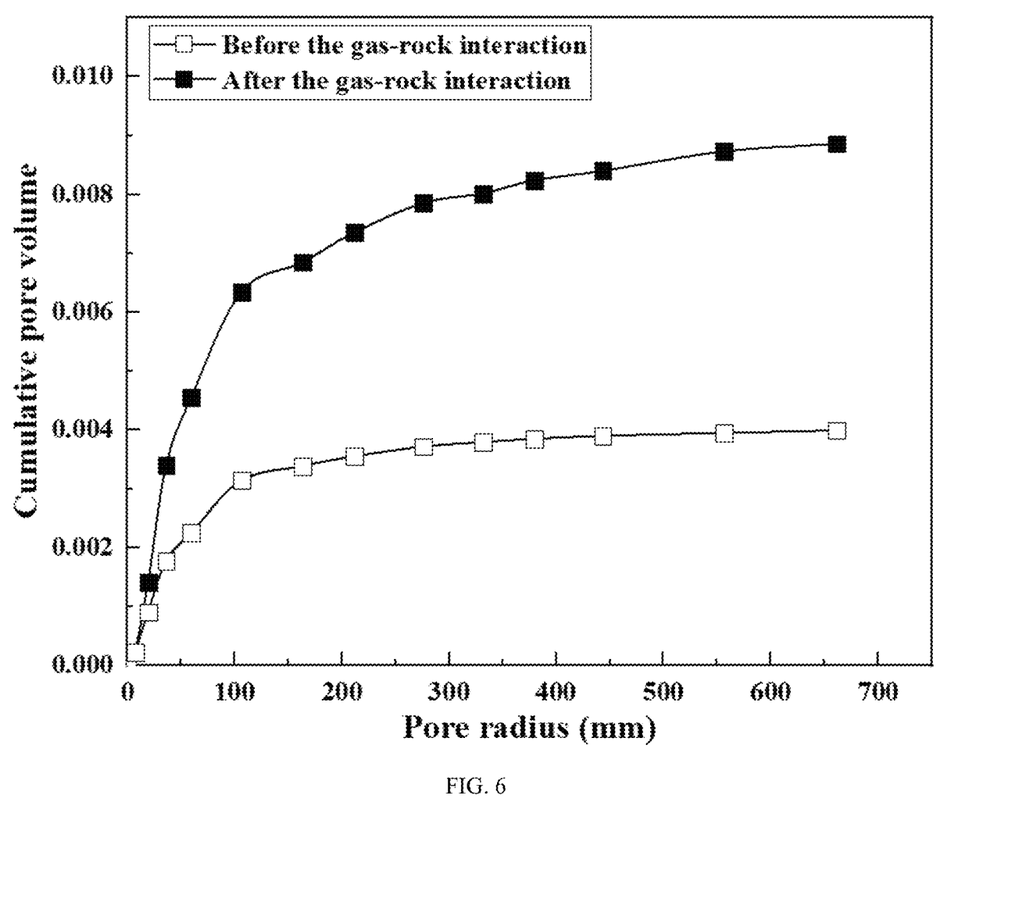
FIG. 6 is a schematic diagram of the porous volume variation of the reduced type after the gas rock reaction.

As shown in FIG. 5 and FIG. 6, the relationship between the porous accumulation volume before the gas rock reaction and the porous radius and the relationship between the porous accumulation volume after the gas rock reaction and the porous radius are shown respectively. The data of the porous volume and the porous radius before and after the reaction can be obtained according to the gas rock reaction test. By analyzing different types of surrounding rock volume variations, it can be seen that after the reaction of the gas with the rock sample, the porous volume variations include an increasing type (FIG. 5) and a decreasing type (FIG. 6). As can be seen from FIG. 5, before the gas rock reaction, the accumulation volume of the surrounding rock porous volume (the accumulation volume of the porous volume) is larger than the accumulation volume of the porous volume after the reaction, which shows that during the reaction, the porous structure is damaged, and the porous size is mainly reduced. From FIG. 6, it can be seen that before the gas rock reaction, the accumulated volume of the surrounding rock porous volume (the accumulated volume of the porous) is less than the accumulated volume of the porous volume after the reaction, which shows that during the reaction process, the porous structure is damaged, the pore size is mainly increased, and part of the surrounding rock matrix is no longer cemented, but it is scattered into micro-nano particles, which increases the porous space. the porous accumulation volume of the final point of each curve is the total porous volume, the final point of the relation curve between the two porous accumulation volumes and the porous radius is solved, and the quotient of the difference value and the initial porous volume before the reaction is the porous volume change rate. It should be noted that the accumulated volume of the porous refers to the sum of the volumes of all the porous smaller than the radius of the corresponding porous. when the radius of the hole is the maximum value, the corresponding accumulated volume of the hole is the total volume of the hole with all radiuses.

The damage degree of the surrounding rock can be evaluated according to the porous volume change rate. For example, in one example, the relationship between the porous volume change rate and the surrounding rock damage degree is shown in Table 2. It should be noted that Table 2 shows the relationship between the rate of change of the porous volume of the surrounding rock and the degree of damage, and does not represent the distribution range of the rate of change of the porous volume of the surrounding rock and the degree of damage.

TABLE 2

| $K_1$ (%) | Damage degree of porous structure |
|---|---|
| $0 < K_1 < 20$ | No |
| $20 \leq K_1 < 40$ | Weak |
| $40 \leq K_1 < 60$ | Strong |
| $60 \leq K_1 < 80$ | Super strong |

Figure 7:
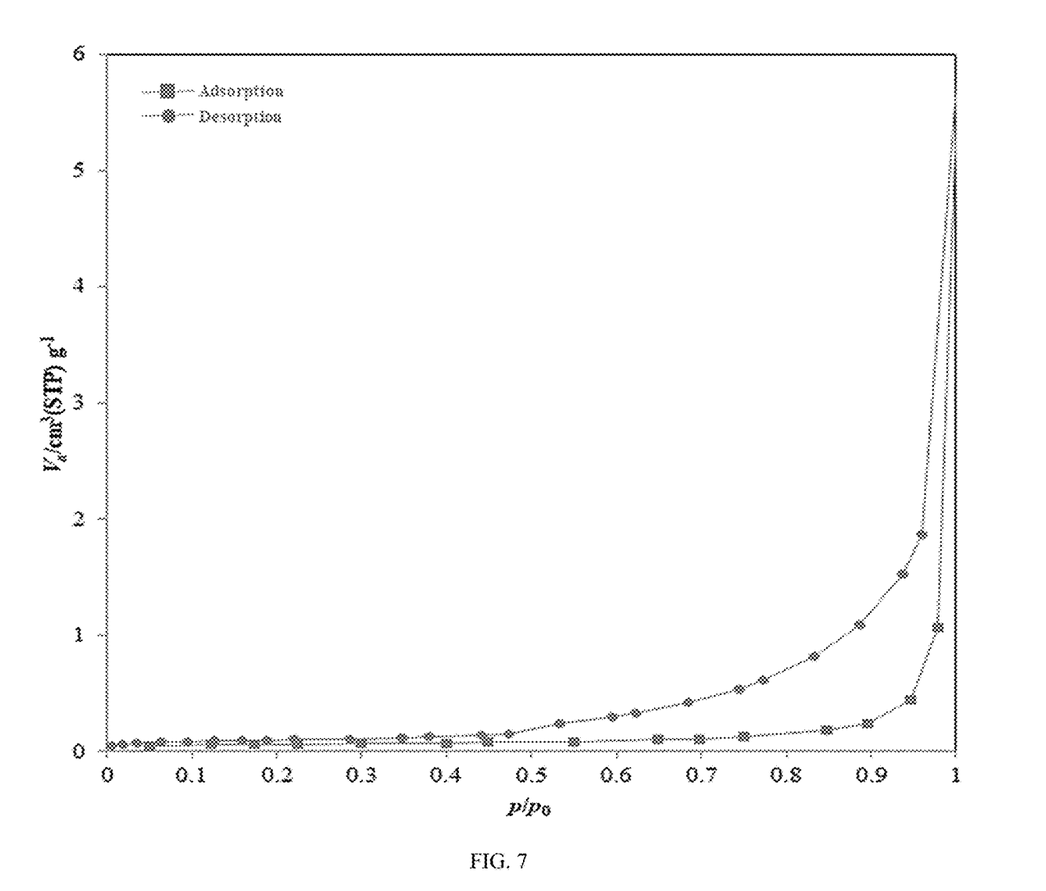
FIG. 7 is an adsorption-desorption curve before the gas rock reaction.
Figure 8:
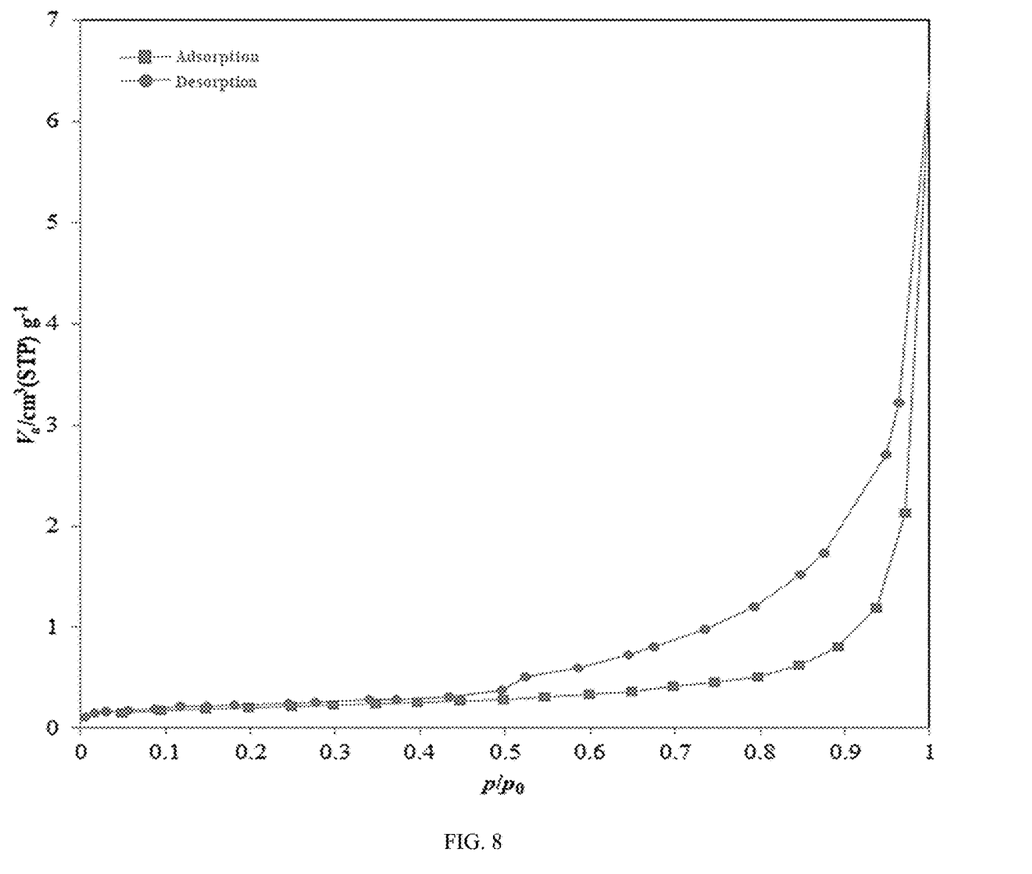
FIG. 8 is an adsorption-desorption curve after gas rock reaction.

In the low-temperature nitrogen adsorption test, not only the porous volume parameter can be obtained, but also the adsorption-desorption curve can be obtained. The morphology of different adsorption-desorption curves may represent different porous types. The adsorption-desorption curve (as shown in FIG. 7) can be obtained before the reaction test between the rock sample and the high-temperature and high-humidity gas. The adsorption-desorption curve (as shown in FIG. 8) can also be obtained after the reaction test of the rock sample and the high-temperature and high-humidity gas. In FIG. 7 and FIG. 8, P is the equilibrium pressure, $P_0$ is the saturated nitrogen pressure, and $P/P_0$ is the data output by the low-temperature nitrogen adsorption device, which is a relative ratio. $V_a$ is the single layer adsorption amount [$cm^3$ $(STP)g^{-1}$], representing the volume of gas molecules that are converted to the standard state covering all solid surfaces. comparing the adsorption-desorption curve shape before and after the gas rock reaction, it can analyze whether the porous type is changed. In comparison with the two groups of adsorption-desorption curves shown in FIGS. 7 and 8, it is found that the adsorption-desorption curves before and after the gas rock reaction have not changed, so it can be known that the porous shape of the corresponding rock sample has not changed. It can be seen that the damage to the porous structure can be evaluated by using the adsorption-desorption curve before and after the gas rock reaction. Therefore, the device and the evaluation method provided by the embodiment of the invention can accurately research the damage of the high-temperature and high-humidity gas to the surrounding rock porous structure in the tunnel excavation.

In the invention, by recovering the stress condition of the surrounding rock of the original tunnel stratum, and ensuring the same temperature condition and gas component of the original stratum, the damage process of the porous structure can be effectively monitored, comprising the front and back changes of the porous diameter, the change of the porous volume, The change of the porous type also realizes the evaluation of the damage degree of the whole porous.

Although preferred embodiments of the present invention have been described, those skilled in the art may make additional changes and modifications to these embodiments once the basic inventive concept is known. Therefore, the appended Claims are intended to be construed as including the preferred embodiments and all changes and modifications falling within the scope of the invention. It will be apparent to those skilled in the art that various changes and modifications may be made to the invention without departing from the spirit and scope of the invention. Thus, if these modifications and variations of the present invention fall within the scope of the appended Claims and their equivalents, the present invention is also intended to encompass these modifications and variations.

The invention claimed is:

1. A method for evaluating a damage to a surrounding rock porous structure due to a high-temperature and high-humidity gas, comprising configuring a device for evaluating the damage to the surrounding rock porous structure by the high-temperature and high-humidity gas, wherein the device comprises: a rock sample clamper, a temperature control device, a pressurizing device, a gas mixing injection device, a computed tomography (CT) scanning device and a low-temperature nitrogen adsorption device;

the rock sample clamper is configured for placing and clamping a rock sample, the rock sample comprises a broken block and a surrounding rock formed by simulating a tunnel excavation, a simulation tunnel is formed between the broken block and the surrounding rock, a simulation excavation cutting line is formed on the surrounding rock;

the temperature control device is configured for providing an in-situ temperature for the rock sample; the pressurizing device is configured for providing an in-situ pressure for the rock sample; the gas mixing injection device is configured for providing an in-situ gas for the rock sample;

the CT scanning device is configured for scanning a rock sample structure before and after a gas injection to visually monitor and analyze a gas transport path and a porous structure change and perform a qualitative evaluation on the damage to the surrounding rock porous structure under an action of the high-temperature and high-humidity gas;

the low-temperature nitrogen adsorption device is configured for performing a low-temperature nitrogen adsorption test on the surrounding rock before and after the gas injection to utilize test data to combine with a fractal theory, to obtain indexes for quantitatively evaluating a damage degree of the surrounding rock porous structure under the action of the high-temperature and high-humidity gas, said indexes including a porous complexity change rate and a porous volume change rate, to perform the qualitative evaluation;

the method comprises:

making the rock sample, comprising: cutting a plunger sample at a centre of a standard rock core, and taking a rest part as a surrounding rock sample; wherein the plunger sample is configured for simulating a broken rock structure in the tunnel excavation, the surrounding rock sample is configured for simulating the surrounding rock in the tunnel excavation, a section between the plunger sample and the surrounding rock sample is configured for simulating a section between a broken rock body and the surrounding rock in the tunnel excavation;

fixing the rock sample in the rock sample clamper;

applying the in-situ temperature and the in-situ pressure to the rock sample, and injecting the in-situ gas, wherein the in-situ gas reacts with the rock sample;

configuring the CT scanning device to visually monitor and analyze the gas transport path in a gas rock reaction and the porous structure change before and after the gas rock reaction to perform the qualitative evaluation on the damage to the surrounding rock porous structure under the action of the high-temperature and high-humidity gas, comprising: configuring the CT scanning device to respectively scan the rock sample before and after the gas rock reaction to obtain a CT scanning image of a cross section of the rock sample along different positions; comparing the CT scanning image of the cross section of the same position of the rock sample before and after the gas rock reaction, obtaining the gas transport path in the gas rock reaction, in the CT scanning image, a gas rock and a surrounding rock skeleton are displayed in different colours, the gas transport path is allowed to be obtained by observing the CT scanning image; according to a gas transport path analysis to obtain the porous structure change before and after the gas rock reaction; qualitatively evaluating the damage to the surrounding rock porous structure under the action of the high-temperature and high-humidity gas according to the porous structure change;

respectively performing the low-temperature nitrogen adsorption test to the surrounding rock before and after the gas rock reaction to obtain a change of the related parameters of the porous structure;

calculating the porous complexity change rate and the porous volume change rate according to the change of the related parameters of the porous structure, and quantitatively evaluating the damage to the surrounding rock porous structure according to the porous complexity change rate and/or the porous volume change rate;

wherein the calculating the porous complexity change rate according to the change of the related parameters of the porous structure comprises applying a first calculation formula defined as:

$$\frac{V}{V_m} = K\left(RT\ln\left(\frac{P_0}{P}\right)\right)^{-(3-D)},$$

$$\sigma_1 = \frac{D_I}{D_E},$$

wherein, in the first calculation formula, V is a gas adsorption volume under a balance pressure P, $V_m$ is a layer of gas adsorption volume, V and $V_m$ are obtained by the low-temperature nitrogen adsorption test, K is characteristic constant, R is gas constant, T is an absolute temperature, $P_0$ is a saturated vapour pressure of nitrogen at a liquid nitrogen temperature, D is a fractal dimension, $\sigma_1$ is the porous complexity change rate, $D_I$ is a fractal dimension before the gas rock reaction, $D_E$ is a fractal dimension after the gas rock reaction, $P_0/P$ is a damage coefficient;

wherein the porous volume change rate is calculated according to the change of the related parameters of the porous structure by applying a second calculation formula defined as:

$$K_1 = \frac{|V_{p1} - V_{p2}|}{V_{p1}} \times 100\%,$$

wherein, in the second calculation formula, $K_1$ is the porous volume change rate, $V_{P1}$ is a porous volume before the gas rock reaction, $V_{P2}$ is a porous volume after the gas rock reaction, $V_{P1}$ and $V_{P2}$ are obtained by the low-temperature nitrogen adsorption test.

2. The method for evaluating the damage to the surrounding rock porous structure due to the high-temperature and high-humidity gas according to claim 1, wherein the device for evaluating the damage to the surrounding rock porous structure by the high-temperature and high-humidity gas further comprises: a tail gas separating device, a gas chromatograph and a conductivity meter, the tail gas separating device is configured for performing a gas-liquid separation on a tail gas, the gas chromatograph is configured for detecting a gas component obtained by the gas-liquid separation, the conductivity meter is configured for detecting a conductivity of the liquid obtained by the gas-liquid separation.

3. The method for evaluating the damage to the surrounding rock porous structure due to the high-temperature and high-humidity gas according to claim 2, wherein the method further comprises:
performing the gas-liquid separation to the tail gas at a tail end to obtain gas and liquid,
detecting the gas component and detecting the conductivity of the liquid.

4. The method for evaluating the damage to the surrounding rock porous structure due to the high-temperature and high-humidity gas according to claim 2, wherein the method further comprises:
configuring the low-temperature nitrogen adsorption test to obtain a gas adsorption-desorption curve before and after the gas rock reaction;
judging a porous type according to a shape of the gas adsorption-desorption curve;
judging a change of a porous shape before and after the gas rock reaction according to the porous type;
evaluating a damage condition of the surrounding rock porous structure according to the change of the porous shape.

* * * * *